United States Patent [19]

Jahn et al.

[11] 4,401,498
[45] Aug. 30, 1983

[54] PROCESS FOR PRODUCING RECIPROCAL ADHESION AT THE INTERFACE BETWEEN TWO CONTACTING LAYERS WITH ALUMINUM HYDROXIDE BEING INCLUDED IN ONE OF SAID LAYERS

[75] Inventors: Ulrich W. K. Jahn; Bernd H. Holzapfel, both of Marburg, Fed. Rep. of Germany

[73] Assignee: A.Kettenbach Fabrik Chemischer Erzeugnisse, Dental-Spezialitäten GmbH & Co. KG., Eschenburg-Eibelshausen, Fed. Rep. of Germany

[21] Appl. No.: 236,012

[22] Filed: Feb. 19, 1981

[30] Foreign Application Priority Data

Jan. 23, 1981 [DE] Fed. Rep. of Germany ....... 3102196

[51] Int. Cl.$^3$ .......................... B29H 5/01; A61C 9/00
[52] U.S. Cl. ............................... 156/307.1; 156/307.3; 156/329; 264/16; 264/255; 264/347; 433/37; 433/214; 524/437
[58] Field of Search ............... 264/129, 219, 225, 236, 264/250, 255, 347, 16–20; 428/447; 525/474, 475, 477; 524/437; 156/308.2, 309.3, 307.1, 329, 307.3, 307.1 UD; 433/214, 37

[56] References Cited

U.S. PATENT DOCUMENTS

| | | | |
|---|---|---|---|
| 2,803,613 | 8/1957 | Kather et al. | 428/447 |
| 3,082,527 | 3/1963 | Nitsche | 433/214 |
| 3,560,244 | 2/1971 | Neuroth | 428/447 |
| 4,062,693 | 12/1977 | Berger | 428/447 |

FOREIGN PATENT DOCUMENTS

| | | | |
|---|---|---|---|
| 778100 | 7/1957 | United Kingdom | 156/329 |
| 851016 | 10/1960 | United Kingdom | 156/329 |

*Primary Examiner*—Willard E. Hoag
*Attorney, Agent, or Firm*—Toren, McGeady and Stanger

[57] ABSTRACT

The invention relates to a process for producing reciprocal adhesion at the interface between two contacting layers of condensation crosslinking and addition crosslinking polysiloxanes, aluminum hydroxide being added to one or both polysiloxane layers prior to crosslinking, so that a firmly adhering joint is obtained.

8 Claims, No Drawings

PROCESS FOR PRODUCING RECIPROCAL ADHESION AT THE INTERFACE BETWEEN TWO CONTACTING LAYERS WITH ALUMINUM HYDROXIDE BEING INCLUDED IN ONE OF SAID LAYERS

BACKGROUND OF THE INVENTION

The invention relates to a process for producing reciprocal adhesion at the interface between two contacting layers, whereof one layer is formed from condensation crosslinking polysiloxane and the other layer is formed from addition crosslinking polysiloxane.

Both the condensation crosslinked and the addition crosslinked silicones are in the present case based on oily polyorganosiloxanes and are reinforced to a greater or lesser extent with fillers, so that they have many uses in a consistency varying from the highly fluid to kneadable, particularly as an impression material for dental purposes. It is also possible to use one of the components as an oil without any filler admixture.

Polyorganosiloxanes which have been conventionally used for many years from the structural chemistry standpoint comprise polydiorganosiloxane chains containing at least two chemically reactive groups with varying spacings or only at the chain ends. In joint reaction with other reactants in the presence of catalysts, these groups lead to bridging between the molecular chains. If elastomer products are formed, this crosslinking is called vulcanization. Depending on the degree of crosslinking, vulcanizates are formed with a greater or lesser elasticity and strength.

There is a fundamental difference between the two vulcanization methods, i.e. the condensation crosslinking and addition crosslinking methods, which are performed at ambient temperature.

Condensation crosslinking is based on the reaction of alpha-omega-dihydroxy-polydiorganosiloxanes with organic silicates. Polydimethyl siloxanoles are mainly used as polyorganosiloxanes in producing elastomers for impressions. Although the corresponding phenyl derivatives are less frequently used, the invention can also be employed in connection therewith.

Methyl silicates, mainly in polymer form, or tetraethyl silicate are mainly used for condensation purposes during which alcohols are split off, whilst linking silicon atoms via oxygen bridges in a known reaction. Often mixtures of both silicates are used. In addition, glycol silicates are used for crosslinking and have special advantages.

Catalysts are added to the crosslinking agents to speed up the reaction. A large number of substances are given for this purpose in literature, but usually organo-tin compounds are used, e.g. tin acetate, tin octoate, or dibutyl tin dilaurate. The vulcanization time can vary from a few minutes to several hours as a function of the reactance and catalysts used.

As a result of condensation polymerization, the vulcanizates gradually shrink to a final state, varying their dimensions at different speeds for three reasons:

1. molecular compression
2. evaporation of the alcohols formed as by-products
3. thermal shrinkage, if the impression is taken at elevated temperature, e.g. when taking an impression in the mouth in the dental field.

As a function of the composition of the vulcanizates, the thermal shrinkage can be 0.1 to 0.3%, if the temperature difference is approximately 14%. It is therefore recommended that these special impressions are kept for at least 30 minutes to 2 hours under ambient climatic conditions before being filled with plaster.

The raw materials and adjuvants for the condensation crosslinking impressions are generally much more advantageous from the cost standpoint than addition crosslinking elastomers. However, the latter are superior to condensation crosslinking materials with regards to the dimensional stability and tensile strength. It is possible to considerably reduce the evaporation tendency of the alcohols contained in the vulcanizate by using suitable additives and/or crosslinking agents, so that the dimensional stability comes close to that of addition crosslinked vulcanizates. Another possibility for reducing shrinkage is to use materials with a limited elastic deformation and then adhering them by means of a strong adhesive to a rigid substrate, e.g. the impression spoon conventionally used in dentistry. Shrinkage is then significantly reduced.

In a practical case, 0.46% was measured with free shrinkage, but only 0.16% when using an adhesive lacquer on a suitable substrate using specification No. 19 of the American Dental Association.

According to the specification, the impression material used had a strain in compression of 1.5%. According to this specification, the quality was largely in accordance with type I of impression materials and was close to that of addition crosslinking materials.

Addition crosslinking RTV silicone elastomers have been used for many years, e.g. when the vulcanizate requires a better tensile strength or shrinkage is to be kept low or a higher Shore hardness A is required, when said characteristics cannot be achieved with comparable condensation crosslinking silicone elastomers. However, the corresponding raw materials are much more expensive.

The requisite reactants are vinyl polydimethyl siloxanes with at least two terminal vinyl groups in the molecule and hydrogen polydimethyl siloxanes. As a function of the molecular structure, the vinyl component or the hydrogen polyorganosiloxane can perform the crosslinking reaction. The hydrogen of the hydrogen component is always transferred to the vinyl groups, the additive bond between the two components being produced whilst dissolving the double bonds. The molecular chains are interlinked, leading to vulcanization.

This reaction is performed in the presence of a platinum catalyst, generally formed from hydrogen chloroplatinic acid or its alcohol or siloxane complexes. The effective quantity is between 5 and 500 ppm, the vinyl component always being added.

It is also known to use rhodium compounds or cobalt carbonyl and manganese carbonyl as catalysts for this purpose.

For dental impression purposes, obviously only platinum compounds are used. However, addition crosslinking systems have only been used for this in the last few years after overcoming serious difficulties (German Pat. No. 2,249,822).

Such platinum catalysts are extremely sensitive to a large number of catalysts poisons, of the type constantly occurring in the environment. Even a trace-wise contact between the platinum-containing materials and the organo-tin catalysts of the condensation crosslinking silicones has a disadvantageous effect. Possibly due to this sensitivity, it was for a long time impossible to give reliably accurate vulcanization times for addition crosslinking silicone systems, because they became constantly slower with the shelf life.

Due to careful processing and selection of the raw materials, the disadvantage of these products has been eliminated to such an extent that they can now be used for dental impressions, where high precision and short vulcanization times are required.

However, difficulties are still caused by the sensitivity of hydrogen polyorganosiloxanes to water. Hydrogen is evolved if there is a weak acid or alkaline reaction. In the presence of hydroxyl group-containing substances or moist calcium sulphate, gas bubbles are formed at the contact surface with the vulcanization products. These bubbles are transferred to the mould material, particularly dental plaster and the mould surface becomes porous, which is highly prejudicial to the further processing in the dental laboratory. Various proposals have been made for obviating this disadvantage of addition crosslinking silicones. Thus, DOS No. 2,926,495 proposes the use of palladium or its alloys, as well as other metals in finely divided form in silicone mixtures. The aforementioned metals absorb the hydrogen. Although the sought objective is achieved, the vulcanizate is naturally more expensive. In addition, these costly metals have to be admixed with the entire vulcanizate, although the desired effect is only required at the surface.

BRIEF SUMMARY OF THE INVENTION

The problem of the present invention is therefore the adhesive joining together in a single layer of condensation crosslinking silicone systems and addition crosslinking silicone systems. Both systems are mixtures which vulcanize at ambient temperature which, after vulcanization, have more or less pronounced or scarcely any elastomeric properties.

It has surprisingly been found that additions of greatly dried aluminium hydroxide have an advantageous influence on these disadvantageous properties of addition crosslinking silicones which vulcanize at ambient temperature and that as a result a novel effect is possible. Thus, the present invention proposes the solving of this problem by a process for producing a reciprocal adhesion at the interface between two contacting layers of organopolysiloxanes, according to which aluminum hydroxide is added to one of the two or both polysiloxane layers prior to crosslinking. The aluminum hydroxide in this case performs a function going well beyond that normally expected of the filler. This could not be foreseen. It was particularly surprising that despite containing a considerable amount of organo-tin catalysts, even condensation crosslinking polydiorganosiloxanole materials form a firm bond with layers of addition crosslinking materials if one or both layers contain aluminum hydroxide. Not the slightest connection occurs if the aluminum hydroxide is absent, with otherwise exactly the same composition of the components.

This leads to important advantages for the practical use of addition crosslinking silicones. It is possible to use the economically more advantageous condensation crosslinking silicones for filling dead spaces having no significance for the impression, so that it is only necessary to use that quantity of the expensive addition crosslinking material which is required for the precise reproduction of the desired details.

In principle, this method has been used as the double impression process for many years in dental impression technology. However, it was only possible to use either condensation crosslinking systems or addition crosslinking systems alone. In both cases, the substrate for the second precision impression was a rigid vulcanizate with Shore A hardnesses between 60 and 90 which, prior to vulcanization, was applied in the form of a putty-type material to the impression spoon coated with an excellently adhering adhesive. Thus, the preliminary impression is taken and it is necessary to await the curing.

The fine impression material is then applied in the form of a highly fluid paste to the preliminary impression and the second or correction impression is taken. Sometimes, the paste is also applied with a syringe. Generally, the highly fluid substances are subject to greater shrinkage.

If the preliminary impression material is as inelastic as possible and adheres firmly enough to the substrate and on waiting for the first part of the shrinkage, particularly the thermal shrinkage, it is possible to produce a firmly adhering second impression with an addition crosslinking silicone, provided that the latter or the preliminary impression material or both contain aluminum hydroxide.

The shrinkage of the impression is much the same as that of addition crosslinking silicones or is slightly higher. The other characteristics of the second layer advantageously correspond to addition crosslinked vulcanizates.

It is unimportant whether both materials are simultaneously cured in reciprocal contact or whether the condensation crosslinking or the addition crosslinking material is vulcanized first. The reciprocal adhesion is the same in all cases. Greater precision is achieved if the condensation crosslinking material is vulcanized first and can shrink sufficiently beforehand.

In cases where no importance is attached to the processing time, the condensation crosslinked vulcanizate can be stored up to the end of the shrinkage period, e.g. 24 hours and can then be combined with the addition crosslinking polysiloxane. It is then economically possible to achieve working results, whose quality and all advantages correspond to the exclusive use of addition crosslinking RTV polyorganosiloxanes, except that the latter are more expensive to use. This process can e.g. be used to advantage in dentistry if a number of casts are to be taken from a master mould. In such cases, it is also necessary to fill numerous dead spaces in the flasks which, with condensation crosslinking silicone, is advantageously performed with the aid of an adhesive, after which the vulcanizate can shrink over night.

It was also surprising that aluminum hydroxide did not assist the tendency of hydrogen polyorganosiloxane to evolve hydrogen in addition crosslinking materials and as was to be expected due to its hydroxyl groups. In fact, it reduced the tendency of the vulcanizates obtained according to the invention to give the mould plaster a bubble-containing, porous surface to such an extent that no bubbles could be discovered in any 4 $cm^2$ mould surface when magnified three times. However, the prerequisite is that the addition vulcanizate contains sufficient aluminum hydroxide. If only the condensation crosslinking layer contains hydroxide in contact with the plaster the addition crosslinked layer can give the condensation crosslinked layer a porous surface. This can be avoided by waiting for a long time until the silicone surface is inactivated.

Advantageously, a silicone impression is rinsed with water or surfactant-containing water and is briefly dried in air. The interfacial tension relative to the mould plaster is consequently reduced and the reproduction of very fine details on the mould is greatly improved.

Surprisingly, there is no danger that the washing process will lead to gas generation from the vulcanizate being induced by the aluminum hydroxide. In fact, the mould surface is completely smooth, particularly if the plaster is vacuum-mixed.

As hitherto, aluminum hydroxide has not been used in addition vulcanizing elastomers, it was to be feared, due to its hydroxyl groups, that it would react with methyl hydrogen polysiloxane, whilst evolving hydrogen. It was all the more surprising that $Al(OH)_3$ could be advantageously used together with addition polymerizing materials, whilst having a number of favourable effects. It was also surprising that the activity of the platinum catalyst was in no way reduced by the aluminum hydroxide. There was no need to increase the platinum quantity with the short reaction times required.

DESCRIPTION OF PREFERRED EMBODIMENTS

Determination of the maximum dimensional change of the specimen combination of addition and condensation polymerized layers The test specimens obtained according to the following examples A and B were tested according to a method consisting of a variation of specification No. 19 of the American Dental Association (A.D.A) and relates to the requirement 3.3.6 for the determination 4.3.9 of the maximum dimensional change. The variation is that the two systems vulcanized on one another are measured as a single test specimen and the latter, together with the condensation polymerized layer adheres immovably to the surface of an aluminium plate.

This takes place in the following way:

1. Treatment of a flat and at least 5 mm thick aluminum plate of minimum size 40×40 mm with an adhesive lacquer with the characteristics given by the manufacturer and of the type conventionally used for silicone rubber.
2. Placing the A.D.A ring mould lubricated according to specification No. 19, 4.3.9 on the adhesive layer of the aluminium plate.
3. Filling the ring mould to a height of max. 3 mm with the mixed condensation polymerizing impression material and pressing the material onto the adhesive layer.
4. This assembly is transferred into a water bath at 32° C. and vulcanized therein for 6.5 minutes. The assembly is then removed, as is the ring mould and within 10 minutes the test specimen is cooled to ambient temperature and allowed to dry completely. The test specimen adheres firmly to the aluminium plate and is ready for the combined vulcanization.
5. In accordance with A.D.A. specification No. 19, 4.3.9 the ring mould is placed on the ruled test block and filled to a height of approximately 2 mm with the mixed addition polymerizing impression material and immediately the specimen with the aluminum plate is pressed onto the material in the mould.
6. The combination, including the aluminum plate and test bar is transferred into the water bath at 32° C. and vulcanization is performed for 90 minutes. The mould and test block are then removed, whilst the test specimen continues to adhere to the aluminum plate.
7. The lines of the test block are well reproduced on the test specimen and are measured after 24 hours according to A.D.A. specification No. 19. The negative dimensional change value is −0.16%, based on the test block line spacing.

EXAMPLE A

1. Condensation crosslinked elastomer
  1.1 Basic paste consisting of
  Dihydroxypolymethyl siloxane of viscosity 18000 $cp_{20}$: 19.7%
  Vaseline DAS 7: 3.0%
  99% aluminum hydroxide of particle size; 1 to 20 microns: 77.3%
  1.2 hardener consisting of
  ortho ethylsilicate: 35%
  Polymethyl silicate: 20%
  Dibutyl tin dilaurate: 45%
  1.3 Elastomer
  The following are homogeneously mixed for 1 minute at ambient temperature:
  Basic paste 1.1: 100 parts
  Hardener 1.2: 0.9 parts
  The rigid paste is forced into the ring mould of the A.D.A. test block to a height of approximately 3 cm, after which the block is placed on the adhesive-treated aluminum plate. The assembly is placed in the water bath at 32° C. The elastomer is completely vulcanized after 6.5 minutes. The aluminum plate with the ring mould and elastomer is cooled for 20 minutes at ambient temperature and dried. The mould is removed. The test specimen is then ready for combined vulcanization with the addition crosslinked elastomer.
2. Addition crosslinked elastomer
  2.1 Basic paste consisting of
  Quartz powder, particle size 0.8 to 20 microns: 45%
  Vinyl methylpolysiloxane with 0.09 millimol of vinyl groups per gram and a viscosity of 8240 $cp_{20}$, containing 50 ppm of catalytically active platinum: 55%
  2.2 Crosslinking agent comprising a methyl hydrogen polysiloxane with a viscosity of approximately 700 $cp_{20}$, containing 3 or more hydride atoms in the molecule and whose reactive SiH proportion is 3 to 3.5 millimol/gram.
  2.3 Elastomer
  The following are mixed for 1 minute at ambient temperature:
  Basic paste 2.1: 20 parts
  Crosslinking agent 2.2: 1 part
  A homogeneous paste is formed and in the manner described hereinbefore is transferred up to a height of approximately 2 mm into the ring mould placed on the ruled test block. The condensation polymerized material is immediately pressed onto the test specimen adhering to the aluminum plate, ensuring a good contact between the elastomers.
  The complete assembly is immediately transferred into the water bath and is vulcanized for 9 minutes at 32° C. The combined specimen is then pressed out of the mould and after 24 hours is measured according to specification No. 19 with the measuring microscope. With respect to the lines of the test block, under these conditions the dimensional change is −0.16%.

EXAMPLE B

1. Condensation crosslinked elastomer.

1.1 Basic paste consisting of:
dihydroxypolydimethylsiloxane of viscosity 18000 $cp_{20}$: 21%
Vaseline DAB 7: 5%
Paraffin oil of viscosity 120 $cp_{20}$: 1%
Quartz powder of particle size 1 to 20 microns: 73%

1.2 Hardener consisting of
ortho ethyl silicate: 35%
Polymethyl silicate: 20%
Dibutyl tin dilaurate: 45%

1.3 elastomer

The following are homogeneously mixed for 1 minute at ambient temperature:
Basic paste 1.1: 100 parts
Hardener 1.2: 0.9 parts The rigid paste is forced into the ring mould of the A.D.A. test block in a layer height of approximately 3 mm, after placing the block on the adhesive-treated aluminum plate. After vulcanizing for 6.5 minutes in the water bath at 32° C. the aluminum plate with the ring mould and elastomer are cooled in air for 20 minutes and dried. The mould is removed. The specimen is thus ready for combining with the addition crosslinking elastomer.

2. Addition crosslinked elastomer.

2.1 Basic paste consisting of
Quartz powder of particle size 0.8 to 20 microns: 45%
Vinyl methylpolysiloxane with 0.09 millimol of vinyl groups/gram and a viscosity of 8000 $cp_{20}$, containing 50 ppm of catalytically active platinum: 55%

2.2 Crosslinking agent paste consisting of a methyl hydrogen polysiloxane of approximate viscosity 700 $cp_{20}$ containing three ore more hydride atoms in the molecule and whose reactive SIH proportion is 3. to 3.5 millimol/gram: 22.22%
99% aluminum hydroxide dried at 120° C.: 70.78%

2.3 Elastomer
At ambient temperature within 1 minute, basic paste 2.1: 54.0 parts
crosslinking agent paste 2.2: 12.3 parts
are mixed to form a homogeneous paste and, in the manner described hereinbefore, the latter is introduced into the ring mould to a height of approximately 2 mm, the mould being placed on the ruled test block. The condensation polymerized specimen on the aluminum plate is pressed onto the paste in such a way that good contact is ensured between the impression materials.

The complete assembly is heated in a water bath at 32° C. for 9 minutes. Following vulcanization, the combined test specimen is forced out of the ring mould and adhering to the aluminum plate the reproduced lines are measured with the measuring microscope after 24 hours in accordance with specification No. 19. Under these conditions and compared with the lines on the test block the dimensional change is −0.16%.

What is claimed is:

1. In a process for producing reciprocal adhesion at the interface between two contacting layers, whereof one layer is formed from condensation crosslinking polysiloxane and the other of said layers is formed from an addition cross-linking polysiloxane, the improvement which comprises adding aluminum hydroxide to at least one of the polysiloxane layers prior to crosslinking.

2. A process according to claim 1, wherein aluminium hydroxide obtained by the wet method by precipitation and dried at temperatures over 80° C. is used.

3. A process according to claim 1, wherein said crosslinking polysiloxanes form elastomers at ambient temperature.

4. A process according to claim 1, wherein one of the two layers is elastic or inelastic and the second layer is elastic.

5. A process according to claim 1, wherein the polysiloxane layer addition crosslinking at ambient temperature is produced in a known manner by a precious metal-catalysed method reaction between vinyl organic polysiloxanes with at least two vinyl groups in the molecule and organohydrogen siloxanes with at least two hydrogen atoms in the molecule connected to silicon atoms.

6. A process according to claim 1, wherein adhesion between the two layers is brought about
(a) in a simultaneous crosslinking process or
(b) in time-succeeding crosslinking processes.

7. A process according to claim 1, wherein the polysiloxane layer condensation crosslinking at ambient temperature is produced in per se known manner by the condensation of chain-like alpha-omega-dihydroxypolydiorganosiloxanes, with organic silicates, accompanied by the catalytic concomitant action of organo-tin compounds.

8. The process of claim 7 wherein the diorganosiloxane is polydimethylsiloxanol and the silicate is polyurethane silicate or tetraethyl silicate.

* * * * *